United States Patent
Gonzales et al.

(10) Patent No.: US 9,616,002 B2
(45) Date of Patent: Apr. 11, 2017

(54) SKIN CLEANSING COMPOSITIONS COMPRISING BIODEGRADABLE ABRASIVE PARTICLES

(71) Applicant: The Procter & Gamble Company, Cincinnati, OH (US)

(72) Inventors: Denis Alfred Gonzales, Brussels (BE); Michael Leslie Groombridge, Prudhoe (GB); Michael McDonnell, Blyth (GB); Stephen Robert Glassmeyer, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/624,477

(22) Filed: Feb. 17, 2015

(65) Prior Publication Data
US 2015/0231042 A1 Aug. 20, 2015

Related U.S. Application Data

(60) Provisional application No. 61/940,496, filed on Feb. 17, 2014.

(51) Int. Cl.
*A61K 8/85* (2006.01)
*A61Q 19/10* (2006.01)
*C11D 9/20* (2006.01)
*A61K 8/02* (2006.01)

(52) U.S. Cl.
CPC .............. *A61K 8/0245* (2013.01); *A61K 8/85* (2013.01); *A61Q 19/10* (2013.01)

(58) Field of Classification Search
CPC ........ A61K 8/0245; A61K 8/85; A61Q 19/10; C11D 3/3715; C11D 9/20
See application file for complete search history.

(56) References Cited

U.S. PATENT DOCUMENTS

| | | | |
|---|---|---|---|
| 5,616,315 | A | 4/1997 | Masterman et al. |
| 6,699,963 | B2 | 3/2004 | Noda et al. |
| 7,393,820 | B2 | 7/2008 | Soldanski et al. |
| 8,329,628 | B2 | 12/2012 | Cervino |
| 8,440,602 | B2 | 5/2013 | Gonzales et al. |
| 8,440,603 | B2 * | 5/2013 | Gonzales ........... C11D 17/0013 510/130 |

(Continued)

FOREIGN PATENT DOCUMENTS

| | | |
|---|---|---|
| JP | 04-331294 A | 11/1992 |
| WO | 2012/177757 A2 | 12/2012 |

OTHER PUBLICATIONS

International Search Report and Written Opinion of the International Searching Authority, Application No. PCT/US2015/014175, mailed May 11, 2015, 9 pages.

*Primary Examiner* — Brian P Mruk
(74) *Attorney, Agent, or Firm* — Betty J. Zea; Steven R. Chuey

(57) ABSTRACT

The present invention relates to a skin cleansing composition, preferably a facial cleanser, comprising biodegradable abrasive particles having a mean Circularity of from about 0.60 to 0.90, a mean Solidity from about 0.60 to about 1.0, and a Biodegradable Rate of at least about 30% as determined after 28 days. In a preferred embodiment, the total skin cleansing composition has a Biodegradable Rate of at least 60% as determined after 90 days.

13 Claims, 3 Drawing Sheets

Leica Z-Stack Image of < 250 μm Fraction of Ground PHBV Particles

Leica Z-Stack Image of 250 μm to 450 μm Fraction of Ground PHBV Particles

(56) References Cited

U.S. PATENT DOCUMENTS

| | | |
|---|---|---|
| 8,445,422 B2 | 5/2013 | Gonzales et al. |
| 8,470,759 B2 * | 6/2013 | Gonzales ............ C11D 17/0013 510/130 |
| 8,629,095 B2 | 1/2014 | Deleersnyder et al. |
| 8,680,036 B2 | 3/2014 | Gonzales et al. |
| 8,703,685 B2 * | 4/2014 | Gonzales ............ C11D 17/0013 510/130 |
| 8,852,643 B2 * | 10/2014 | Gonzales ................. A61Q 5/02 424/401 |
| 8,968,787 B2 | 3/2015 | Gittleman |
| 2004/0136940 A1 | 7/2004 | Lazarowitz |
| 2011/0150787 A1 | 6/2011 | Gonzales et al. |
| 2011/0150788 A1 | 6/2011 | Gonzales et al. |
| 2011/0150951 A1 | 6/2011 | Gonzales et al. |
| 2011/0262504 A1 | 10/2011 | Deleersnyder et al. |
| 2012/0066851 A1 | 3/2012 | Gonzales et al. |
| 2012/0071379 A1 | 3/2012 | Gonzales et al. |
| 2012/0071380 A1 | 3/2012 | Gonzales et al. |
| 2012/0317736 A1 * | 12/2012 | Gonzales ............ C11D 17/0013 15/104.93 |
| 2012/0321567 A1 | 12/2012 | Gonzales et al. |
| 2012/0321568 A1 | 12/2012 | Gonzales et al. |
| 2013/0039961 A1 | 2/2013 | Gonzales et al. |
| 2013/0072417 A1 | 3/2013 | Perez-Prat Vinuesa et al. |
| 2013/0219643 A1 | 8/2013 | Gonzales et al. |
| 2013/0317736 A1 | 11/2013 | Fernandes et al. |
| 2014/0026916 A1 * | 1/2014 | Havens .................... A61K 8/85 132/200 |
| 2014/0105831 A1 | 4/2014 | Gonzales et al. |
| 2014/0352721 A1 | 12/2014 | Gonzales et al. |
| 2014/0352722 A1 | 12/2014 | Gonzales et al. |
| 2014/0357544 A1 | 12/2014 | Gonzales et al. |
| 2015/0007399 A1 | 1/2015 | Gonzales et al. |
| 2015/0007400 A1 | 1/2015 | Gonzales et al. |

* cited by examiner

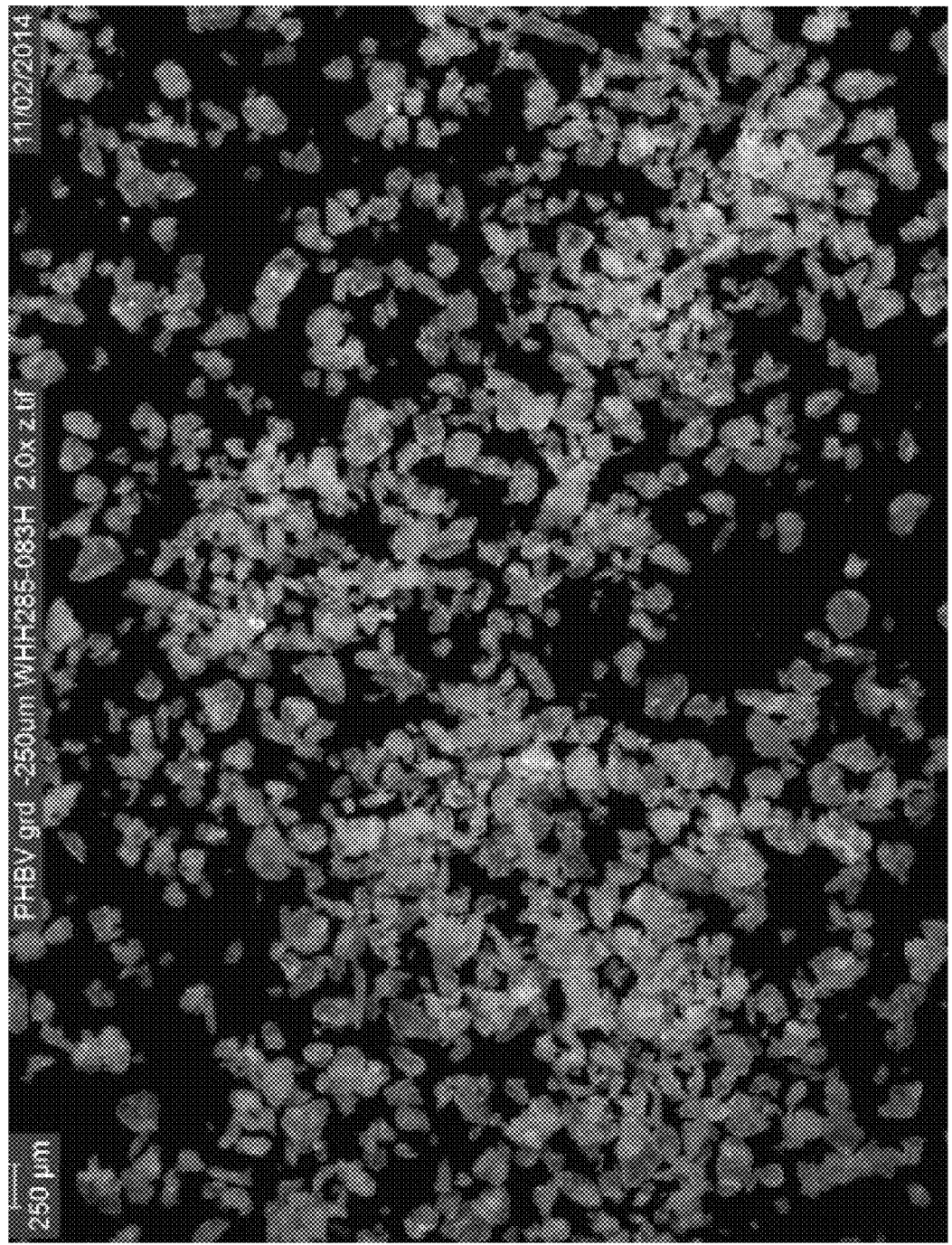
Figure 1A - Leica Z-Stack Image of < 250 μm Fraction of Ground PHBV Particles

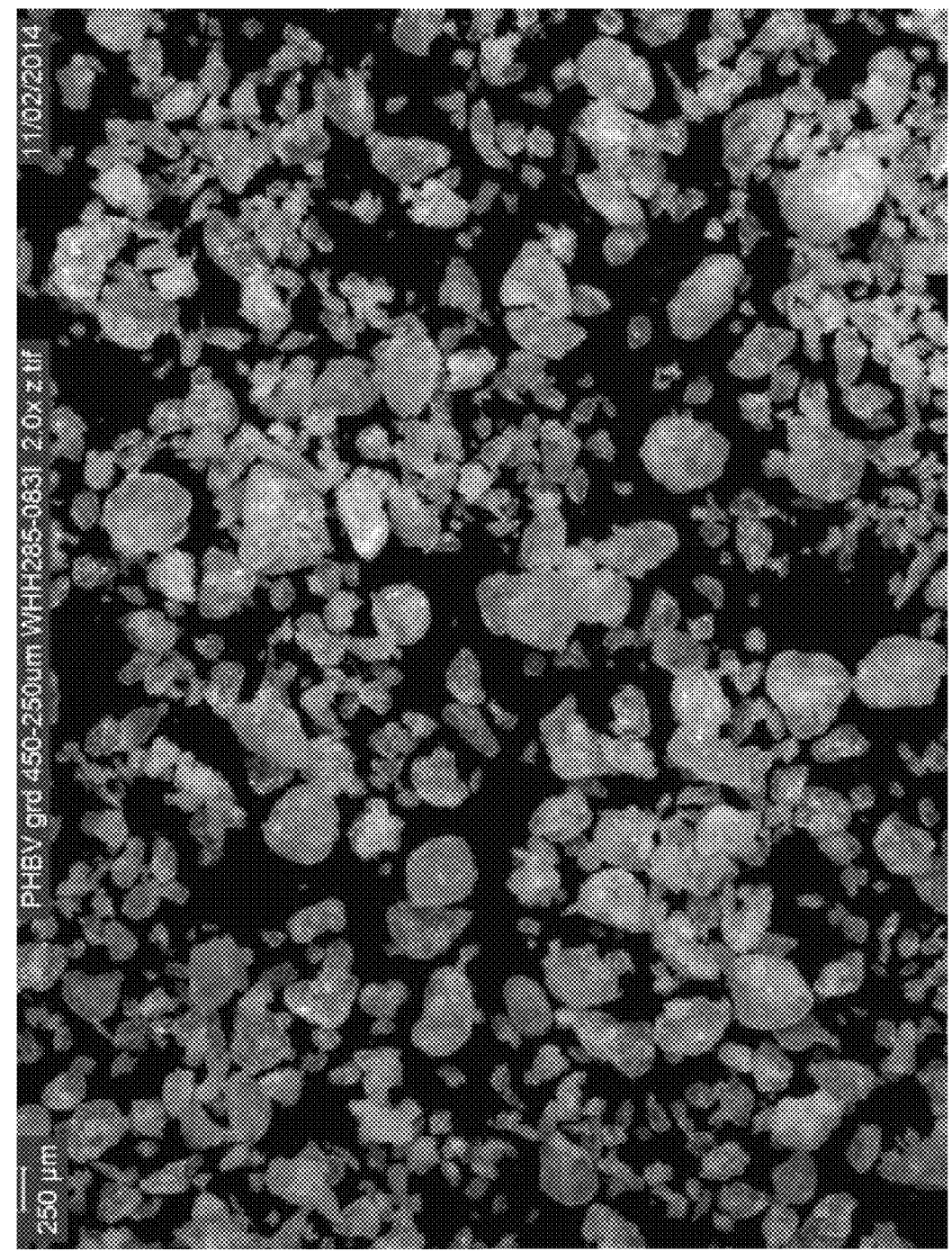
Figure 1B – Leica Z-Stack Image of 250 μm to 450 μm Fraction of Ground PHBV Particles

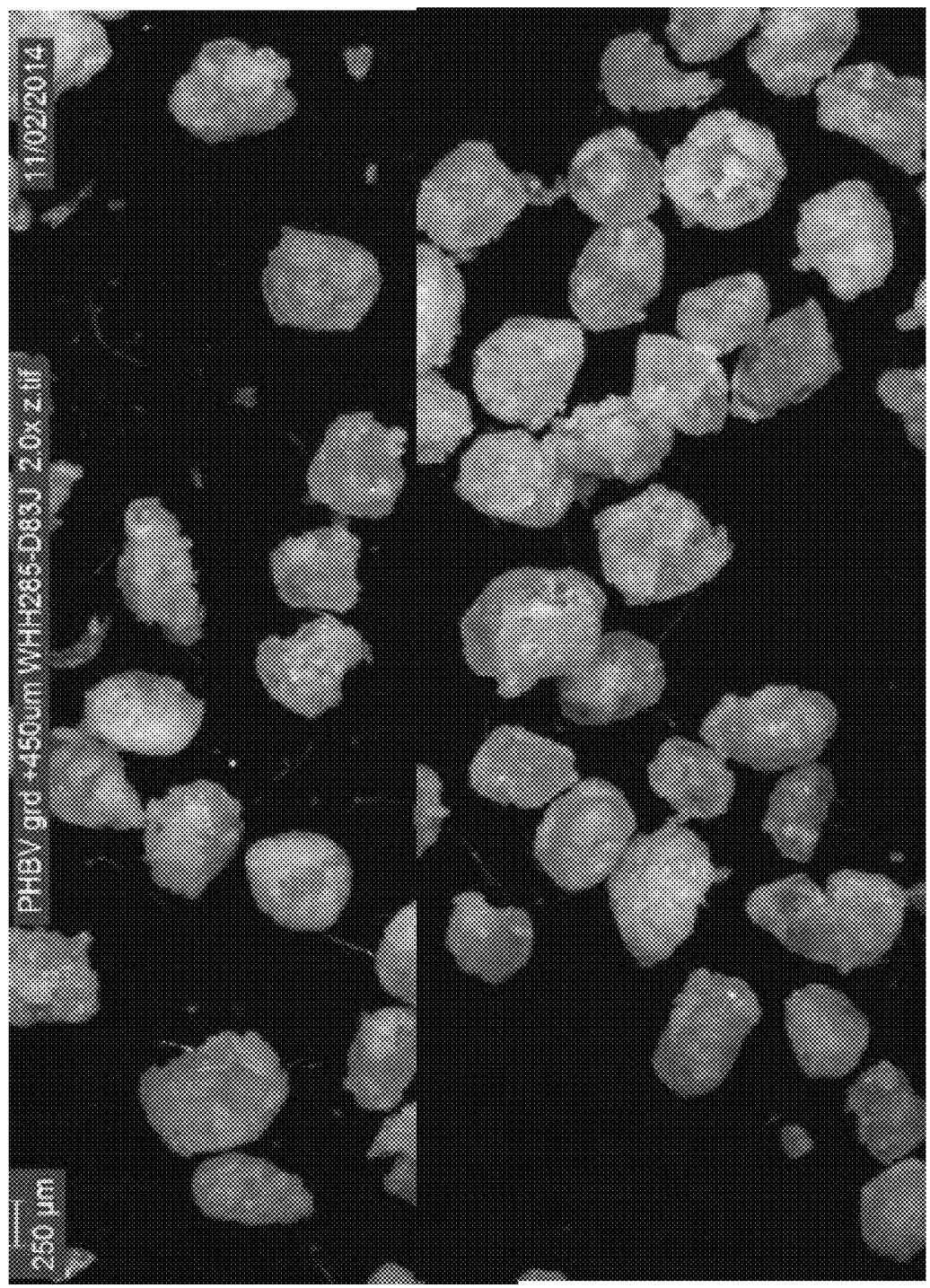
Figure 1C – Leica Z-Stack image of > 450 μm Fraction of Ground PHBV Particles

SKIN CLEANSING COMPOSITIONS COMPRISING BIODEGRADABLE ABRASIVE PARTICLES

FIELD OF THE INVENTION

The present invention relates to a skin cleansing composition comprising biodegradable abrasive particles, and methods of making and using same.

BACKGROUND OF THE INVENTION

Skin cleansing compositions routinely include abrasive particles for a variety of reasons such as cleansing the skin (e.g., removal of dirt, sebum, or oil) or improving the appearance of the skin (e.g., exfoliation). Abrasive particles are commonly made from petroleum-based synthetic polymers like polystyrene or cross-linked styrene (XST) and/or polyurethane (PU), polyolefins plastic or waxes, etc. Unfortunately, these petroleum-based synthetic polymers may pose long-term disposal problems and could have adverse effects on the environment. On the other hand, natural abrasives like abrasives derived from plants or shells e.g.: from nuts or otherwise abrasive based on mineral material, present poor aesthetic and/or potential allergenic issues or are too abrasive for usage onto facial skin.

Recently, biobased polymers like polyhydroxy alkonates (PHA) have attracted significant attention because they are made from renewable resources (e.g., plants), and can be recycled using biological processes (i.e., biorenewable or biodegradable) to reduce greenhouse gas emission and conserve limited resources. On account of the current market demands for more green alternatives, the consumer goods industry has started to use biobased polymers as abrasive particles in fabric and home care products for cleaning dishes, clothes, and hard surfaces (see for example US2013/317736 (P&G) and JP 04-331294 (Three Bond)).

The use of biobased polymers as abrasive particles (i.e., "biodegradable abrasive particles") in skin cleansing compositions, particularly facial cleansers, has remained largely unexplored.

Existing biodegradable abrasive particles of the types disclosed in JP 04-331294 were designed for certain fields of application (e.g., hard surface cleaning, detergents for dish or clothes) which require scouring of stains, preferably hard to remove stains or soils, deposited on inanimate surfaces. Reapplication of the same biodegradable abrasive particles for use in skin cleansing composition would not be appropriate, as they tend to be overly abrasive and can damage the skin, especially when applied on facial skin surface, which is more sensitive.

Conversely, less aggressive biodegradable abrasive particles may yield poor and/or inadequate cleansing performance as evidenced by soil or make-up remaining on the skin after use. Furthermore, existing biodegradable abrasive particles often have an undesirable texture for skin cleansing compositions. For example, consumers selecting a facial cleanser may avoid compositions that feel gritty or overly coarse or succetible to create allergenic reaction for instance, but not limited to natural exfoliant containing protein. Formulators often must choose between overly abrasive particles that may cause damage on the skin surface, and gentler abrasive particles with a better sensorial feel but with reduced, perhaps inadequeate, cleansing efficacy. In addition, such currently known biodegradable abrasive particles are not selected for various stability, aesthetics, and/or compatibility with other materials commonly present in the personal care composition field and therefore would likely not be considered dermatologically acceptable.

Therefore, there is a need for a new skin cleansing composition, preferably a facial cleansing composition, comprising biodegradable abrasive particles, having skin cleansing and/or exfoliating benefits when applied on skin surfaces, preferably facial skin surfaces. There is also the need for a new skin cleansing composition, preferably a facial cleansing composition, having a sufficiently acceptable surface safety profile and is dermatologically acceptable. It is also highly desirable that the total skin cleansing composition is biodegradable, preferably in addition to the abrasive particles being biodegradable.

SUMMARY OF THE INVENTION

The present invention is directed to a skin cleansing composition comprising biodegradable abrasive particles present at a level of from about 0.1 wt % to about 10 wt %, preferably from about 0.3 wt % to about 8 wt %, more preferably from about 0.5 wt % to about 5 wt %, or even more preferably from about 1 wt % to about 3 wt %, and a dermatologically acceptable carrier, wherein wt % is relative to the total weight of the composition. The abrasive particles of the present invention have: i) a mean Circularity of from about 0.60, 0.65, or 0.70 to about 0.80, 0.85 or 0.90, or preferably from about 0.65 to about 0.85, as determined according to ISO 9726-6:2008; ii) a mean Solidity from about 0.60, 0.65, 0.70, or 0.75 to about 9.0, 9.5, or 1.0, or preferably from about 0.85 to about 1.0, as determined according to ISO 9276-6:2008; and iii) a Biodegradable Rate from of at least about 30%, or about 35%, or about 40%, as determined after 28 days according to the Biodegradability Test as disclosed herein. In an embodiment, the skin cleansing composition has a Biodegradable Rate of at least about 60%, or about 70%, or about 80%, or about 90%, as determined after 90 days according to the Biodegradability Test as disclosed herein.

In another aspect, the present invention relates to a method for cleansing a human's skin surface comprising topically contacting the skin surface with a skin cleansing composition according to the present invention, and additionally followed by a rinsing step. It is an advantage of the compositions according to the present invention that they may be used to clean/cleanse facial skin surfaces, whilst providing a good surface safety profile. A further advantage of the present invention is that in the compositions herein, the abrasive particles can be formulated at very low levels, whilst still providing the above benefits.

In another aspect, the present invention relates to use of biodegradable abrasive particles in a skin cleansing composition of the present invention, for delivering a benefit selected from the group consisting of mild skin exfoliation, dirt removal from a skin surface, and combinations thereof. These and other aspects of the present invention will become more apparent upon reading the following drawings and detailed description of the invention.

BRIEF DESCRIPTION OF THE DRAWINGS

FIGS. 1A, B and C are electron microscopy images showing the biodegradable abrasive particles of the present invention.

DETAILED DESCRIPTION OF THE INVENTION

Except as otherwise noted, the articles "a", "an", and "the" mean "one or more."

The term "comprising" means that other steps and other ingredients which do not affect the end result can be added, and this term encompasses the terms "consisting of" and "consisting essentially of". The compositions and methods/processes of the present invention can comprise, consist of, and consist essentially of the essential elements and limitations of the invention described herein, as well as any of the additional or optional ingredients, components, steps, or limitations described herein. Particularly, the compositions of the present invention contain biodegradable abrasive particles, and one or more additional or optional ingredients as described hereinafter.

All percentages, parts and ratios are based upon the total weight of the compositions of the present invention, unless otherwise specified. All such weights as they pertain to listed ingredients are based on the active level and, therefore do not include carriers or by-products that may be included in commercially available materials. The components, including those which may optionally be added, as well as methods for preparation, and methods for use, are described in detail below.

All ratios are weight ratios unless specifically stated otherwise. All temperatures are in Celsius degrees (° C.), unless specifically stated otherwise.

As used herein "biodegradable" means chemical dissolution of the organic material by bacteria or other biological means at a certain rate (%) or above according to the Biodegradability Test as described in the Method Section herein.

As used herein "Biodegradable Test" means the test as described in the Method Section herein in which the test material is suspended in a phosphate buffered media containing an activated sludge inoculum and the formation of carbon dioxide measured via an electrolytic respirometer. The test material is the sole carbon and energy source and under aerobic conditions microorganisms metabolize organic substances producing $CO_2$ as the ultimate product.

As used herein "derivatives" means an ester, ether, amide, hydroxyl, and/or salt structural analogue of the relevant compound.

As used herein "dermatologically acceptable" means that the compositions or components described are suitable for use in contact with human skin tissue, preferably facial skin surfaces, without undue toxicity, incompatibility, instability, allergic response, discomfort, and the like.

As used herein "exfoliation" or "mild skin exfoliation" means removal of dead skin cells from the outermost layer of the skin whilst minimizing the risk of over-exfoliating the skin, which may otherwise result in damaged and/or redness to the skin, or discomfort to the user.

As used herein "surface safety profile" means that the compositions or components thereof are not overly abrasive to human skin tissue, particularly human facial skin tissue, so as to not scratch or damage the surface (e.g., redness) while still providing a good cleaning performance on the skin surface.

Skin Cleansing Compositions

The present invention is directed to a skin cleansing composition comprising: biodegradable abrasive particles present at a level of from about 0.1 wt % to about 10 wt %, preferably from about 0.3 wt % to about 8 wt %, more preferably from about 0.5 wt % to about 5 wt %, or even more preferably from about 1 wt % to about 3 wt %, and a dermatologically acceptable carrier, wherein the wt % is relative to the total weight of the composition.

The skin cleansing compositions according to the present invention are designed as skin cleansers for a variety of human skin surfaces. Examples of the skin cleansing compositions include, a facial cleanser, a body wash, a hand cleanser, or a body cleanser. In a preferred embodiment, the skin cleansing compositions herein are suitable for use as a facial cleanser.

In a preferred embodiment, the skin cleansing compositions according to the present invention are considered "biodegradable" as determined by the Biodegradability Test as disclosed in the Method Section herein. Biodegradation is the chemical dissolution of materials by bacteria or other biological means. Currently, biodegradability is commonly associated with environmentally friendly products that are capable of decomposing back into natural elements. Organic material can be degraded aerobically with oxygen, or anaerobically without oxygen. Readily biodegradable materials discussed herein are material which biodegrade according to protocol and requirement described in Biodegradability Test as disclosed in the Method Section here. This Biodegradability Rate would include all components except for inorganic materials and water.

In one embodiment, the term "biodegradable" in reference to the skin cleansing compositions means a skin cleansing composition having a Biodegradability Rate of at least about 60%, preferably at least about 70%, more preferably at least about 80%, or even more preferably at least 90%, as determined after 90 days according to the Biodegradability Test as disclosed herein. In another embodiment herein, the Biodegradable Rate of the skin cleansing composition is at most about 100%, 99%, 95%, 90%, 85% or 80%.

In another embodiment, the skin cleansing compositions have a viscosity in the range of from about 100 cps to about 1,000,000 cps, preferably from about 1,000 to about 300,000 cps, or more preferably from about 5,000 to about 200,000 cps. The viscosity are measured at 20 $sec^{-1}$ and 20° C. with a Rheometer, model AR 1000 (Supplied by TA Instruments) with a 4 cm conic spindle in stainless steel, 2° angle (linear increment from 0.1 to 100 $sec^{-1}$ in max. 8 minutes).

In another embodiment, the skin cleansing compositions herein are neutral compositions. In other preferred embodiments, the skin cleansing compositions herein have a pH in the range of from about 5.0 to about 6.0, more preferably from about 5.5 to about 7.5, wherein the pH is measured at 25° C.

Accordingly, the skin cleansing compositions herein may comprise suitable bases and acids to adjust the pH. A suitable base to be used herein is an organic and/or inorganic base. Suitable bases for use herein are the caustic alkalis, such as sodium hydroxide, potassium hydroxide and/or lithium hydroxide, and/or the alkali metal oxides such, as sodium and/or potassium oxide or mixtures thereof. A preferred base is a caustic alkali, more preferably sodium hydroxide and/or potassium hydroxide.

Other suitable bases include ammonia, ammonium carbonate, all available carbonate salts such as $K_2CO_3$, $Na_2CO_3$, $CaCO_3$, $MgCO_3$, etc., alkanolamines (e.g., monoethanolamine), urea and urea derivatives, polyamine, etc. Typical levels of such bases, when present, are from about 0.01 wt % to about 5.0 wt %, preferably from about 0.05 wt % to about 3.0 wt %, and more preferably from about 0.1 wt % to about 0.6 wt %, wherein the wt % is relative to the total weight of the composition.

The skin cleansing compositions herein may comprise an acid to trim its pH to the required level, despite the presence of an acid, if any, the skin cleansing compositions herein will maintain their preferred neutral, pH as described herein above. A suitable acid for use herein is an organic and/or an inorganic acid. A preferred organic acid for use herein has a pKa of less than 6. A suitable organic acid is selected from the group consisting of citric acid, lactic acid, glycolic acid, succinic acid, glutaric acid and adipic acid and a mixture thereof. A mixture of the acids may be commercially available from BASF under the trade name Sokalan® DCS. A suitable inorganic acid is selected from the group consisting hydrochloric acid, sulfuric acid, phosphoric acid and a mixture thereof. A typical level of such an acid, when present, is from about 0.01 wt % to about 5.0 wt %, preferably from about 0.04 wt % to about 3.0 wt % and more preferably from about 0.05 wt % to about 1.5 wt %, wherein the wt % is relative to the total weight of the composition.

Carrier

The skin cleansing composition may comprise a dermatologically acceptable carrier. Dermatologically acceptable carriers may be selected for various stability, aesthetics, and/or compatibility with other materials present in the skin cleansing composition. Suitable carriers include water and/or water soluble solvents. The skin cleansing composition may comprise from about 1% to about 95% by weight of water and/or water equivalent solvent. The composition may comprise from about 1%, 3%, 5%, 10%, 15%, 20%, 25%, 30%, 35%, 40%, 45%, 50%, 55%, 60%, 65%, 70%, 75%, 80%, 85%, or 90% to about 90%, 85%, 80%, 75%, 70%, 65%, 60%, 55%, 50%, 45%, 40%, 35%, 30%, 25%, 20%, 15%, 10%, or 5% water and/or a water-equivalent solvent. "Water-equivalent solvent" refers to a compound which has a similar ability as water to solubilize a material. Suitable water-equivalent solvents include monohydric alcohols, dihydric alcohols, polyhydric alcohols, glycerol, glycols, polyalkylene glycols such as polyethylene glycol, and mixtures thereof. Particularly suitable solvents, include lower aliphatic alcohols such as ethanol, propanol, butanol, isopropanol; diols such as 1,2-propanediol, 1,3-propanediol, butanediol, pentanediol, hexanediol, heptanediol, decanediol; glycerin; water, and mixtures thereof. In certain embodiments, the skin cleansing composition comprises water, diols, glycerin, and combinations thereof.

Suitable carriers also include oils. The skin cleansing composition may comprise from about 1% to about 95% by weight of one or more oils. Oils may be used to solubilize, disperse, or carry materials that are not suitable for water or water-equivalent solvents. Suitable oils include silicones, hydrocarbons, esters, fatty amides, ethers, and mixtures thereof. Oils may be fluid at room temperature. However, certain skin cleansing product forms (i.e., solid or semisolid stick) may require non-fluid oils. The oils may be volatile or nonvolatile. "Non-volatile" means a material that exhibits a vapor pressure of no more than about 0.2 mm Hg at 25° C. at one atmosphere and/or a material that has a boiling point at one atmosphere of at least about 300° C. "Volatile" means that the material exhibits a vapor pressure of at least about 0.2 mm. of mercury at 20° C. Volatile oils may be used to provide a lighter feel when a heavy, greasy film is undesirable.

Suitable oils include volatile oils. In certain embodiments, the volatile oils may have a viscosity ranging from about 0.5 to about 5 centistokes 25° C. Volatile oils may be used to promote more rapid drying of the skin care composition after it is applied to skin. Non-volatile oils are also suitable for use in the composition. Non-volatile oils are often used for emolliency and protective properties. Non-volatile oils preferably may have a viscosity ranging from about 5 to about 800,000 est (or greater) or from about 20 to about 200,000 est. Suitable examples of oils for use in the skin cleansing composition of the present invention are found in US2013/039961 (P&G).

Structuring Agent

The skin cleansing composition may comprise a structuring agent. Structuring agents may be used to increase viscosity, thicken, solidify, or provide solid or crystalline structure to the skin cleansing composition. The structuring agent may be used to suspend or disperse the abrasive particles. Structuring agents are typically grouped based on solubility, dispersibility, or phase compatibility. Examples of aqueous or water structuring agents include polymeric agents, natural or synthetic gums, polysaccharides, and the like. In one embodiment, the composition may comprise from about 0.0001%, 0.001%, 0.01%, 0.05%, 0.1%, 0.5%, 1%, 2%, 3%, 5% to about 25%, 20%, 10%, 7%, 5%, 4%, or 2%, by weight of the composition, of one or more structuring agents. Suitable examples of structuring agents for use in the skin cleansing composition of the present invention are found in US2013/039961 (P&G).

Optional Skin Cleansing Ingredients

The skin cleansing composition may comprise one or more optional components to provide an efficacious and/or consumer desirable product. For example, the composition can include other actives or agents. For instance, suitable optional actives and agents may include an active or agent selected from a group consisting of sugar amines, vitamins, oil control agents, photosterols, hexamidine compounds, tightening agents, anti-wrinkle actives, anti-atrophy actives, flavonoids, N-acyl amino acid compounds, retinoids, peptides, UV actives, photostabilizers, anti-cellulite agents, desquamation actives, anti-acne actives, anti-oxidants, radical scavengers, conditioning agents, anti-inflammatory agents, tanning actives, skin lightening agents, antiperspirant actives, sensates, anti-dandruff actives, anti-melanogenic agent, sebum secretion inhibitors, blood circulating facilitating agent, softeners, keratine protecting agents, emollients, moisturizers, and combinations thereof.

Method of Using the Skin Cleansing Compositions

The present invention encompasses a method for cleansing a human's skin surface comprising topically contacting the skin surface with a skin cleansing composition according to the present invention. Suitable skin surfaces herein include body, hands, and facial skin surfaces.

In a preferred embodiment, the composition according to the present invention is topically applied to the facial skin surface. "Facial skin surface" refers to one or more of the forehead, periorbital, cheek, perioral, chin, and nose skin surfaces.

The composition herein may be in its neat form or in its diluted form. By "in its neat form", it is to be understood that the composition is applied directly onto the skin surface to be treated without undergoing any dilution. By "diluted form", it is meant herein that the composition is diluted by the user typically with water. The composition is diluted prior to use to a typical dilution level of up to 10 times its weight of water. As usually recommended dilution level is a 10% dilution of the composition in water.

The composition herein may be applied using the palms of the hands and/or fingers, or using an appropriate implement, such as a cloth, sponge, mask, razor, wand, cotton ball, swab, or pad, soaked in the diluted or neat composition herein. Furthermore, once applied onto the skin surface the composition may be agitated over the skin surface.

The method herein may optionally contain an additional rinsing step, preferably after the application of the composition. By "rinsing", it is meant herein contacting the surface cleaned/cleansed with the method according to the present invention with substantial quantities of appropriate solvent, typically water, directly after the step of applying the liquid composition herein onto the skin surface. By "substantial quantities", it is meant herein between 0.001 L and 1 L of water per $m^2$ of skin surface, more preferably between 0.1 L and 1 L of water per $m^2$ of skin surface.

Biodegradable Abrasive Particles

The skin cleansing compositions herein comprises biodegradable abrasive particles that are selected or synthesized to possess the desired shapes, as defined by certain parameters, such as for non-limiting example: Circularity, Solidity, and/or adequate hardness, to be effective for cleansing skin surfaces. In an embodiment, the biodegradable abrasive particles have an acceptable surface safety profile and thus are not overly abrasive on contact with skin. In another embodiment, the biodegradable abrasive particles are dermatologically acceptable.

The term "biodegradable" in reference to the abrasive particles, means that the abrasive particles of the present invention have a Biodegradability Rate of at least about 30%, preferably at least about 35%, or more preferably at least about 40%, as determined after 28 days according to the Biodegradability Test as disclosed herein. In a preferred embodiment, the Biodegradable Rate of the abrasive particles is at most about 100%, 99%, 95%, 90%, 85% or 80%.

The biodegradable abrasive particles are selected from the group of polymeric material consisting of:
(a) one or more homo-polymers or co-polymers selected from the group consisting of polyhydroxy alkanoate (PHA), polylactic acid derivatives (PLA), polycaprolactone (PLC), poly(glycolic acid) (PGA), and blends thereof;
(b) aliphatic and/or, aromatic co-polyesters, preferably wherein said co-polyester is selected from co-polyester containing succinic, adipic, terepthalic diacids, propanediol, butanediol, pentanediol monomer or blends thereof, preferably polybutylene succiate (PBS), or polybutylene-adipate-terephtalate (PBAT);
(c) starch, thermoplastic starch (TPS), or blends thereof;
(d) thermoplastic cellulose (TPC) derivative selected from the group consisting of cellulose ester, cellulose ether, cellulose alkanoate and blends thereof, preferably said thermoplastic cellulose is cellulose acetate, nitrocellulose or blends thereof; and
(e) combinations of (a) to (d).

In a preferred embodiment, the polymeric material is polyhydroxy alkanoate (PHA) selected from the group consisting of poly-3-hydroxybutyrate (PHB), poly-3-hydroxyhexanoate, poly-3-hydroxy-valerate, poly-3-hydroxy-butyrate-co-3-hydroxyvalerate (PHBV), poly-3-hydroxybutyrate-co-3-hydroxyhexanoate, and blends thereof.

In a preferred embodiment, the biodegradable abrasive particle of the present invention are poly-3-hydroxybutyrate-co-3-hydroxyvalerate (PHBV). PHBV polymers can replace conventional thermoplastic used for packaging. PHBVs are biopolymers that are synthesized by bacteria as intracellular carbon and energy storage granules under limited nutrients in the presence of excess carbon source. The molecular weight of these polymer varies from 200 KDa to 3,000 KDa depending on the microorganism, nutrients and growth conditions. The molecular weight of PHBV polymers ranges from 1,000 g/mol to 3,000,000 g/mol, preferably from 20,000 g/mol to 700,000 g/mol, more preferably from 100,000 g/mol to 500,000 g/mol.

In certain embodiments, the biodegradable abrasive particle of the present invention are reduced into particles from polymeric foam material, as described above, by grinding or milling. Biodegradable abrasive particles may also contain minor components of process aids well known in the art, such as crystal nucleating agents, anti-oxidants, stabilizers, and rheology modifiers. In an embodiment the biodegradable polymer is blended with abundant amount of mineral or vegetable and soluble or insoluble filler. Inclusion of a large quantity of filler helps break the polymer into abrasive particles and features biodegradable particles with large surface areas (e.g., via porosity and capillarity) which enhance the degradation kinetics. This is especially the case when the filler is water soluble. Typical fillers suitable for use with PHBV polymers are minerals (e.g., metal chlorides such as for example, NaCl, KCl, etc.; metal carbonates such as for example, $Na_2CO_3$, NaHCO, etc.; metal sulfates such as for example, $MgSO_4$), generally all mineral adsorbents provide hardness, which is compatible with the overall target hardness of the biodegradable abrasive cleaning particle.

The filler can also be derived from vegetal feedstock, essentially from cellulose or lignocelluloses based material (e.g., nut shell, wood or bamboo fibers, corn cob, rice hull, etc. including carbohydrates such starch and flour, xanthan gum, alginic, dextran, agar, and the like). The suitable fillers are also biodegradable and do not change the biodegradability of the final abrasive particles or biodegradability of the skin cleansing composition.

Typical biodegradable PHBV polymers comprise filler from about 10 wt % to 70 wt %, preferably from 20 wt % to 60 wt %, or most preferably from 40 wt % to 50 wt %, wherein wt % is relative to the total weight of the PHBV polymer materials.

The applicant have surprisingly found that biodegradable abrasive particles according to the present invention, when formulated into the skin cleansing compositions, provide good cleaning/cleansing performance on human skin surfaces, whilst providing a good surface safety profile. In particular, the inventors have found that by controlling the shapes of the biodegradable abrasive particle, through selection or synthesis, to be non-rolling and not overly sharp, it would then deliver a benefit selected from the group consisting of mild skin exfoliation, good dirt removal from a skin surface, and combinations thereof, preferably without damaging the skin surface or causing discomfort to the users to provide a acceptable surface safety profile. By "non-rolling", it is meant that the abrasive particles slide across the skin surface rather than roll across the surface. It is believed that this non-rolling character promotes improved cleansing efficacy and exfoliation benefits.

The shapes of the biodegradable abrasive particle can be defined in various ways. The present invention defines effective shapes, for example, by mean Circularity, and mean Solidity. The present invention defines the shapes of the biodegradable abrasive particle in the form of particles, which reflects the geometrical proportions of a particle and more pragmatically of the particle's population. Analytical techniques allow an accurate simultaneous measurement of particle shapes from a large number of particles, typically greater than 1,000, preferably greater than 10,000 particles (more preferably above 100,000 particles). This enables accurate tuning and/or selection of average particle population shape with discriminative performance. These measurement analyses of particle shape are conducted using on Occhio Nano 500 Particle Characterisation Instrument with its accompanying software Callistro version 25 (Occhio s.a.

Liege, Belgium) or the latest version available. This instrument is used to prepare, disperse; image and analyse the particle samples, as per manufacturer's instructions, and the following instrument setting selections: White Requested=180, vacuum time=5,000 ms, sedimentation time=5,000 ms, automatic threshold, number of particles counted/analyses=8,000 to 500,000, minimum number of replicates/sample=3, lens setting 1×/1.5×.

Circularity

The term "Circularity" means a quantitative, 2-dimensional image analysis shape description and is being measured according to ISO 9276-6:2008(E) section 8.2 as implemented via the Occhio Nano 500 Particle Characterisation Instrument with its accompanying software Callistro version 25 (Occhio s.a. Liege, Belgium) or the latest version available. Circularity is a preferred Mesoshape descriptor and is widely available in shape analysis instrument such as in Occhio Nano 500 or in Malvern Morphologi G3. Circularity is sometimes described in literature as being the difference between a particle's shape and a perfect sphere. Circularity values range from 0 to 1, where a circularity of 1 describes a perfectly spherical particles or disc particle as measured in a two dimensional image.

$$C = \sqrt{\frac{4\pi A}{P^2}}$$

Where A is projection area, which is 2D descriptor and P is the length of the perimeter of the particle.

By the term "mean Circularity" the applicant considers the average of the circularity values of each particle taken from a population of at least 1,000, preferably above 10,000 particles, preferably above 50,000 particles, more preferably above 100,000 particles, after excluding from the measurement and calculation, the circularity of particles having area-equivalent diameter (ECD) of below 10 micrometers. Mean data are extracted from volume-based vs. number-based measurements.

The applicant has found that the biodegradable abrasive particles having a mean Circularity to meet the surface safety criteria and promote effective skin cleansing from about 0.60, 0.65, or 0.70 to about 0.80, 0.85 or 0.90. In certain embodiment, the abrasive particles have a mean Circularity of about 0.65 to about 0.85, as determined according to ISO 9726-6:2008(E) section 8.2. Alternatively, the biodegradable abrasive particles have a mean Circularity of between about 0.60 and about 0.90, or preferably between about 0.65 and about 0.85, as determined according to ISO 9726-6:2008(E) section 8.2.

Solidity

The term "Solidity" means a quantitative, 2-dimensional image analysis shape description, and is being measured according to ISO 9276-6:2008(E) section 8.2 as implemented via the Occhio Nano 500 Particle Characterisation Instrument with its accompanying software Callistro version 25 (Occhio s.a. Liege, Belgium). The non-spherical particle herein has preferably at least one edge or surface having a concave curvature. Solidity is a mesoshape parameter, which describes the overall concavity of a particle/particle population. Solidity values range from 0 to 1, where a solidity number of 1 describes a non-concave particle, as measured in literature as being:

$$Solidity = A/Ac$$

Where A is the area of the particle and Ac is the area of the convex hull (envelope) of bounding the particle.

By the term "mean Solidity" the applicant considers the average of the solidity or roughness values of each particle taken from a population of at least 1,000, preferably above 10,000 particles, preferably above 50,000 particles, more preferably above 100,000 particles, after excluding from the measurement and calculation, the solidity or roughness data of particles having area-equivalent diameter (ECD) of below 10 micrometers. Mean data are extracted from volume-based vs. number-based measurements.

The applicant has found out that biodegradable abrasive particles having a defined mean Solidity from about 0.60, 0.65, 0.70, or 0.75 to about 0.90, 0.95, or 1.0. In certain embodiment, the biodegradable abrasive particles have a mean Solidity from about 0.85 to about 1.0, as determined according to ISO 9276-6:2008(E) section 8.2. Alternatively, the biodegradable abrasive particles have a mean Solidity of between from about 0.60 to about 1.0 or preferably from about 0.85 to about 1.0, as determined according to ISO 9276-6:2008(E) section 8.2.

The term "Solidity" is sometime also named "Convexity" in literature or in some apparatus software using the solidity formula in place of its definition described in ISO 9276-6 (convexity=Pc/P where P is the length of the perimeter of the particle and Pc is length of the perimeter of the convex hull—envelope—bounding the particle). Despite solidity and convexity being similar mesoshape descriptor in concept, the applicants refer herein to the solidity measure expressed above by the Occhio Nano 500, as indicated above.

Hardness

The biodegradable abrasive particles should be hard enough to provide good cleaning/cleansing performance while providing good surface safety and/or skin feel acceptability. The biodegradable abrasive particles in the present invention may have Shore® D hardness from about 35, 40, 45, or 50 durometer to about 60, 65, or 75 durometer as determined according to ASTM D2240-05 (2010). Shore® D hardness measurement is carried out by using an ASTM durometer, such as the Type D Style Durometer available from Pacific Transducer Corp. of Los Angeles, Calif., or from ELECTROMATIC Equipment Co., Inc. 600 Oakland Ave Cedarhurst, N.Y. 11516 (description of the stylus digital or gauge instrument at http://www.checkline.com/durometers)

Mean Particle Size

The applicant has found that good skin cleansing efficiency can be achieved with the biodegradable abrasive particles having a certain mean particle size as defined by their area-equivalent diameter (ISO 9276:2008(E) section 7) also called Equivalent Circle Diameter ECD (ECD) (ASTM F1877-05 Section 11.3.2). Mean ECD of particle population is calculated as the average of respective ECD of each particles of a particle population of at least 1,000, preferably above 10,000 particles, preferably above 50,000 particles, more preferably above 100,000 particles after excluding from the measurement and calculation the data of particles having area-equivalent diameter (ECD) of below 10 micrometers. Mean data are extracted from volume-based vs. number-based measurements. In an embodiment, biodegradable abrasive particles have a mean particle size as expressed by the area-equivalent diameter of from about 10 µm, 50 µm, or 100 µm to about 200 µm, 350 µm, or 1,000 µm, or preferably from about 150 µm to about 250 µm.

FIG. 1A-1C show ground PHBV biodegradable abrasive particles. The PHBV particles have a mean ECD<250 µm, 250 to 450 μm, >450 μm, respectively, and having mean Circularity from 0.60 to 0.90 according to the present invention.

Typical shearing or graining methods to reduce the above material in biodegradable abrasive powder featuring useful shape defined by the targeted circularity range, so other preparation e.g.: grain shaping methods described in the art may be employed such as agglomerating, printing, carving, etc. As examples, suitable way of reducing the biodegradable abrasive material into abrasive cleaning particles herein is to grind or mill the material using jaw Crushers mills or rotor mills or cutting or blade or knife mills, or impact or rotor or disc mills suchs as manufactured by Retschz (see http://www.retsch.com/products/milling). If needed the temperature need to be kept constant during the griding operation, whereas suitable grinding temperature should not exceed 60° C. In most cases, the optimal grinding temperature needs to be below 30° C., sometimes below 0° C. and in cases grinding is better achieved in cryogenic condition using refrigerant media such as $CO_2$ or nitrogen in liquid conditions.

Other suitable means include the use of eroding tools such as a high speed eroding wheel with dust collector wherein the surface of the wheel is engraved with a pattern or is coated with abrasive sandpaper or the like to promote to form the abrasive cleaning particles herein.

Alternatively the abrasive raw material can be broken into pieces of a few cm dimensions by manually chopping or cutting, or using a mechanical tool such as a lumpbreaker, for example the Model 2036 from S Howes, Inc. of Silver Creek, N.Y.

Preferably, the abrasive cleaning particles obtained via grinding or milling operation are single particles.

Previous shaping processes are sometimes facilitated by mixing previous biodegradable abrasive materials as fillers within a thermoplastic or solidifying matrix. Such processes e.g.: including selection of matrix and respective load of filler are well known in art. In order to achieve precisely the desired shape of the particle, a convenient way is to achieve particles matching effective circularity range consists at foaming the biodegradable abrasive raw material per se or biodegradable abrasive material dispersed within a matrix and reducing the achieved foam into biodegradable abrasive particles with improved efficiency. Foaming processes and foam structure are typically achieved via gas expansion process, e.g.: either by injecting gas or solvent within the biodegradable abrasive precursor and allowing expansion by pressure drop and/or increasing of temperature e.g.: extrusion foaming process or more conveniently with in-situ generated gas followed by hardening of the biodegradable abrasive precursor e.g.: polyurethane foaming process. Alternatively, foam structures can also be achieved via emulsion process, followed by hardening and drying step.

In a highly preferred embodiment herein, in order to achieve the geometrical shape descriptors of the biodegradable abrasive cleaning particles (i.e. circularity, solidity) the biodegradable abrasive cleaning particles are obtained from foamed polymeric material, which is reduced into the biodegradable abrasive particles preferably by grinding or milling as described herein later on.

The applicant has found that gentle cleaning will be achieved with the biodegradable abrasive particles, which have been made from a foam having density above 200 $Kg/m^3$, preferably above 400 $Kg/m^3$ and even more preferably above 600 $Kg/m^3$ since the particle after grinding will have shape with lower angularity, while the applicant has surprisingly found that significantly better skin cleaning effect can be achieved with the foam density being below 200 $Kg/m^3$, more preferably from 25 $Kg/m^3$ to 50 $Kg/m^3$ since the particle after grinding will have shape with higher angularity. In practive, the applicant found that a good compromise is to obtain particle from grinding polymeric foam with density ranging 100 $Kg/m^3$ to 400 $Kg/m^3$.

Test Methods i) Cleansing Efficacy

The cleansing efficacy of the skin cleansing composition comprising the biodegradable abrasive particles can be tested according to the following method. The volar forearm of a test subject is marked into four 4 cm×3 cm sites. Makeup (i.e., Elizabeth Arden Flawless Finish Sponge-on Cream Makeup—warm beige) is applied to each of the four sites. For each site, apply the makeup by dosing a makeup sponge by swiping the sponge across the makeup three times with moderate pressure. Swipe the loaded sponge across a test site three times (with moderate pressure) keeping makeup inside of site. Allow the makeup to dry for 5 minutes. Cleanse one site with an exemplary formulation. Approximately 0.50 $cm^3$ of the exemplary cleanser product is applied to the test site. Rub the cleanser within the site using the index and middle fingers together in a circular/up and down motion for 15 seconds. Rinse the site under running water while rubbing with the index and middle fingers together in a circular motion/up and down motion for 10 seconds. Gently pat the site dry with paper towels taking care not to remove any makeup residue. Allow the site to air dry for 5 minutes. The makeup residue on the test site is removed by using a clean cotton round (e.g., Johnson's Pure Cotton Cosmetic Rounds from Johnson & Johnson) dosed with 1,000 uL of a make-up remover (e.g., Lancome Bi-Facil makeup remover). Swipe the test site with the dosed pad twice by wrapping pad around middle finger holding firmly in place with the index and third finger. Turn pad 180° and swipe the test site twice in a direction perpendicular to the first two swipes. Color values of the residual makeup collected on the cotton round is analyzed using a chromameter (e.g., Minolta Chromameter CR-200). Measurements are taken at the center of the cotton round where the residual makeup was collected. Obtained three measurements of color values of $L^*$, $a^*$, and $b^*$ for each cotton round. Calculate an average delta E (i.e., total color difference). A High Delta E value indicates more residue left on the skin by the product and a low Delta E value indicates low makeup residue. Sensory feel data is subjective evaluation of the texture of the examples.

ii) Biodegradability

The biodegradability of the skin cleansing composition comprising the biodegradable abrasive particles or the biodegradable abrasive particles can be tested according to the following method. This biodegradability test is based on the Organization for Economic Co-operation and Development (OECD) 301B $CO_2$ evolution biodegradation test method that screens chemicals for ready biodegradability in an aerobic aqueous medium.

In this test the test substance is suspended in a phosphate buffered media containing an activated sludge inoculums and the consumption of oxygen and/or the formation of carbon dioxide is measured via an electrolyctic respirometer. The test substance is the sole carbon and energy source and under aerobic conditions microorganisms metabolize organic substances producing $CO_2$ as the ultimate product. The test can run for 28 days or 90 days.

Exemplary Skin Cleansing Compositions

These following compositions were made by mixing the listed ingredients in the listed proportions (weight %) below. Mixing may be done by devices and techniques known in the art. Examples 1-8 herein are meant to exemplify the present invention but are not necessarily used to limit or otherwise define the scope of the present invention. Abrasive particle used in the examples below were grounded from granules or foams of rigid PHBV.

Facial Cleanser Compositions:

| % Weight | Ex. 1 | Ex. 2 | Ex. 3 |
|---|---|---|---|
| Acrylates Copolymer* 1 | 1.50 | 2.0 | — |
| Acrylates/$C_{10}$-$C_{30}$ alkyl acrylate crosspolymer* 2 | — | — | 1.0 |
| Sodium Lauryl Sulfate | 2.0 | — | — |
| Sodium Laureth Sulfate | 8.0 | — | — |
| Ammonium Lauryl Sulfate | — | 6.0 | — |
| Sodium Trideceth Sulfate | — | — | 2.5 |
| Sodium Myristoyl Sarcosinate | — | 2.0 | 2.5 |
| Sodium Lauroamphoacetate* 3 | — | — | 5.0 |
| Sodium Hydroxide* | pH > 6 | — | — |
| Triethanolamine* | — | pH > 6 | pH 5.2 |
| Cocamidopropyl Betaine | 4.0 | 7.0 | — |
| Glycerin | 4.0 | 5.0 | 2.0 |
| Sorbitol | — | — | 2.0 |
| Salicylic Acid | — | — | 2.0 |
| Fragrance | 0.1 | 0.1 | 0.1 |
| Preservative | 0.3 | 0.3 | 0.15 |
| PEG 120 Methyl Glucose Trioleate* 4 | 0.5 | — | 0.25 |
| PEG 150 Pentaerythrityl Tetrastearate* 5 | — | 0.40 | — |
| Citric Acid** | pH 5.5 | pH 5.5 | pH 5.5 |
| Biodegradable abrasive particles made from PHBV Y1000P granules (Tianan Biologic Materials Co., Ningbo, China) | 0.5 Circularity: 0.65 Solidity: 0.95 Size: 200 μm | 1.0 Circularity: 0.75 Solidity: 0.9 Size: 200 μm | 3.0 Circularity: 0.65 Solidity: 0.95 Size: 150 μm |
| Water | Balance | Balance | Balance |

*per the supplier use directions, the base is used to activate the acrylates copolymer
**acid can be added to adjust the formula to a lower pH
1. Carbopol Aqua SF-1 ® from Noveon™.
2. Carbopol Ultrez 21 ® from Noveon™.
3. Miranol ® Ultra L32 from Rhodia.
4. Glucamate LT ® from Chemron.
5. Crothix ® from Croda.

For Examples 1-3, add Carbopol® to de-ionized free water of the formulation. Add all surfactants except cationics and betaines. If the pH is less than 6 then add a neutralizing agent (typically a base, i.e., Triethanolamine, sodium hydroxide) to adjust to a pH greater than 6. If necessary, apply gentle heat to reduce viscosity and help minimize air entrapment. Add betaine and/or cationic surfactants. Add remaining ingredients and if desired reduce the pH with an acid (i.e., citric acid) and increase viscosity by adding sodium chloride.

Body Wash Compositions:

| % Weight | Ex. 4 | Ex. 5 | Ex. 6 |
|---|---|---|---|
| Glycerin | 0.8 | 0.8 | 0.8 |
| Guar hydroxypropyl-trimonium chloride (N-Hance 3196, Aqualon) | 0.7 | 0.7 | 0.7 |
| PEG 90M (Polyox WSR 301, Amerchol Corp.) | 0.2 | 0.2 | 0.2 |
| Citric Acid | 0.4 | 0.4 | 0.4 |
| Miracare SLB-365 (Rhodia, Inc.: Sodium Trideceth Sulfate, Sodium Laurampho-acetate, Cocamide MEA) | 23.7 | 23.7 | 23.7 |
| Fragrance | 1.4 | 1.4 | 1.4 |
| Soybean oil | 5.0 | 5.0 | 5.0 |
| Sodium chloride | 3.5 | 3.5 | 3.5 |
| Preservatives | 0.45 | 0.45 | 0.45 |
| NaOH or citric acid | pH 6.2 | pH 6.2 | pH 6.2 |
| Zero shear viscosity, Pa-sec | 6,530 | 6,530 | 6,530 |
| Biodegradable abrasive particles made from PHBV Y1000P granules (Tianan Biologic Materials Co., Ningbo, China) | 3.0 Circularity: 0.85 Solidity: 0.90 Size: 150 μm | 5.0 Circularity: 0.85 Solidity: 0.95 Size: 100 μm | 10.0 Circularity: 0.80 Solidity: 0.95 Size: 300 μm |
| Water | Balance | Balance | Balance |

The cleansing phase can be prepared by conventional formulation and mixing techniques. Prepare the cleansing phase by first adding water, skin benefit components, and thickeners into a mixing vessel and agitate until a homogeneous dispersion is formed. Then add in the surfactants, Disodium EDTA, preservative and half the sodium chloride and all other ingredients, except fragrance and the withheld sodium chloride. Maintain at ambient temperature while agitating the mixing vessel. In a separate vessel, pre-wet the structuring polymers with fragrance and add to the mix vessel at the same time as the remaining sodium chloride while agitating. Add the soybean oil. Keep agitation until homogeneous, and then pump through a static mixing element to disperse any polymer lumps to complete the batch.

Body Cleanser Compositions:

| % Weight | Ex. 7 | Ex. 8 |
| --- | --- | --- |
| Cocoamidopropyl betaine | 5.15 | 5.15 |
| Sodium Laureth Sulfate | 5.8 | 5.8 |
| Sodium Lauroyl Sarcosinate | 0.5 | 0.5 |
| Polyquaternium 10 | 0.1 | 0.1 |
| $C_{12}$-$C_{14}$ fatty alcohol | 0.45 | 0.45 |
| Zinc Stearate | 1.5 | 1.5 |
| Glycol Disterate | 0.25 | 0.25 |
| Sodium Lauryl Sulfate | 0.53 | 0.53 |
| Lauramide Diethanolamide | 0.48 | 0.48 |
| Sodium Sulfate | 0.05 | 0.05 |
| Citric Acid | 0.05 | 0.05 |
| DMDM hydantoin (1,3-Dimethylol-5,5-dimethylhydantoin Glydant) | 0.2 | 0.2 |
| Tetra Sodium EDTA | 0.1 | 0.1 |
| Fragrance | 0.5 | 0.5 |
| Polysacchardie (Xanthan Gum-glyoxal modified Optixan-T) | 0.2 | 0.2 |
| Biodegradable abrasive particles made from PHBV foam using Y1000P (Tianan Biologic Materials Co., Ningbo, China) and achieving the foam density 150 Kg/m³ via extrusion foaming | 0.5 Circularity: 0.65 Solidity: 0.95 Size: 200 μm | 1.0 Circularity: 0.80 Solidity: 0.95 Size: 150 μm |
| Water | Balance | Balance |

For Examples 7-8, in a suitable vessel, the ingredients are combined and mixed (with heat if needed) until uniform. The composition may be warmed to dissolve all ingredients. Once the composition is uniform, the product is poured into suitable containers. Examples 7-8 may be used as body cleansing composition.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:
1. A skin cleansing composition comprising:
   a) abrasive particles present at a level of from about 0.1% to about 10%, by weight of the composition, wherein said abrasive particles comprise:
      i) a mean Circularity of from about 0.65 to about 0.90, as determined according to ISO 9726-6:2008;
      ii) a mean Solidity from about 0.60 to about 1.0, as determined according to ISO 9276-6:2008;
      iii) a Biodegradable Rate of about 30% to about 100%, as determined after 28 days according to the Biodegradability Test as disclosed herein; and
      iv) a mean particle size as expressed by the area-equivalent diameter greater than 450 μm according to ISO 9276-6:2008;
   b) a structuring agent; and
   c) a dermatologically acceptable carrier;
   wherein the composition comprises a viscosity from about 1000 cps to about 300,000 cps.
2. The skin cleansing composition according to claim 1 wherein said skin cleansing composition has a Biodegradable Rate of about 60% to about 100%, as determined after 90 days according to the Biodegradability Test as disclosed herein.
3. The skin cleansing composition according to claim 1, wherein said abrasive particles have a mean particle size as expressed by the area-equivalent diameter of from about 450 μm to about 1,000 μm.
4. The skin cleansing composition according to claim 1, wherein said abrasive particles have a Hardness of from about 35 to about 75 durometer as determined according to ASTM D2240-05 (2010).
5. The skin cleansing composition according to claim 1, wherein said abrasive particles are selected from the group of polymeric material consisting of:
   (a) one or more homo-polymers or co-polymers selected from the group consisting of polyhydroxy alkanoate (PHA), polylactic acid derivatives (PLA), polycaprolactone (PLC), poly(glycolic acid) (PGA), and blends thereof;
   (b) aliphatic and aromatic co-polyesters selected from co-polyester containing succinic, adipic, terepthalic diacids, propanediol, butanediol, pentanediol monomer or blends thereof;
   (c) starch, thermoplastic starch (TPS), or blends thereof;
   (d) thermoplastic cellulose (TPC) derivative selected from the group consisting of cellulose ester, cellulose ether, cellulose alkanoate and blends thereof; and
   (e) combinations of (a) to (d).
6. The skin cleansing composition according to claim 5, wherein said polymeric material is polyhydroxy alkanoate (PHA) selected from the group consisting of poly-3-hydroxybutyrate (PHB), poly-3-hydroxyhexanoate, poly-3-hydroxy-valerate, poly-3-hydroxy-butyrate-co-3-hydroxyvalerate (PHBV), poly-3-hydroxybutyrate-co-3-hydroxyhexanoate, and blends thereof.
7. The skin cleansing composition according to claim 6, wherein said polymeric material is poly-3-hydroxy-butyrate-co-3-hydroxyvalerate (PHBV).

8. The skin cleansing composition according to claim 1, wherein said skin cleansing composition has a viscosity in the range of from about 5,000 cps to about 200,000 cps.

9. The skin cleansing composition according to claim 1, wherein said skin cleansing composition has a pH in the range of from about 5 to about 8.

10. The skin cleansing composition according to claim 1, wherein said skin cleansing composition is selected from the group consisting of a facial cleanser, body wash, hand cleanser and body cleanser.

11. The skin cleansing composition according to claim 1, wherein said skin cleansing composition further comprises one or more actives selected from the group consisting of sugar amines, vitamins, oil control agents, photosterols, hexamidine compounds, tightening agents, anti-wrinkle actives, anti-atrophy actives, flavonoids, N-acyl amino acid compounds, retinoids, peptides, UV actives, photostabilizers, anti-cellulite agents, desquamation actives, anti-acne actives, anti-oxidants, radical scavengers, conditioning agents, anti-inflammatory agents, tanning actives, skin lightening agents, antiperspirant actives, sensates, anti-dandruff actives, anti-melanogenic agent, sebum secretion inhibitors, blood circulating facilitating agent, softeners, keratin protecting agents, emollients, moisturizers, and combinations thereof.

12. The skin cleansing composition according to claim 1, wherein said skin cleansing composition further comprises thickening or suspending agents.

13. A method for cleansing or exfoliating a human's skin surface comprising contacting said skin surface with a skin cleansing composition according to claim 1, wherein said skin cleansing composition is a facial cleanser and is topically applied onto said skin surface of a face, and additionally followed by a rinsing step.

* * * * *